United States Patent [19]

Belanger et al.

[11] 4,332,807

[45] Jun. 1, 1982

[54] N-SUBSTITUTED-BENZYL-11-ENDO-AMINO-5,6,7,8,9,10-HEXAHYDRO-2-HYDROXY (OR METHOXY)-6,9-METHANOBENZOCY-CLOOCTENE (OR NONENE) CENTRALLY-ACTING ANALGESICS

[75] Inventors: Patrice C. Belanger, Dollard des Ormeaux; Robert N. Young, Senneville, both of Canada

[73] Assignee: Merck & Co., Inc., Rahway, N.J.

[21] Appl. No.: 228,449

[22] Filed: Jan. 26, 1981

[51] Int. Cl.[3] .................... A61K 31/40; A61K 31/13; A61K 31/275; C07C 87/28
[52] U.S. Cl. .............................. 424/274; 260/465 E; 424/304; 424/330; 564/337; 564/384; 564/389; 564/391; 564/392; 548/482
[58] Field of Search ............... 260/465 E, 326.1; 424/304, 330, 274; 564/384, 337, 389, 391, 396

[56] References Cited

U.S. PATENT DOCUMENTS

| | | | |
|---|---|---|---|
| 3,499,906 | 3/1970 | Robinson et al. | 260/293.4 |
| 3,513,169 | 5/1970 | Robinson et al. | 260/294.7 |
| 3,514,463 | 5/1970 | Robinson et al. | 260/294.7 |
| 3,700,734 | 10/1972 | Robinson et al. | 260/293.54 |
| 3,836,670 | 9/1974 | Freed et al. | 424/330 |
| 4,001,331 | 1/1977 | Freed et al. | 260/571 |
| 4,076,953 | 2/1978 | Freed et al. | 560/142 |

FOREIGN PATENT DOCUMENTS 54-128600 10/1979 Japan .

*Primary Examiner*—Dolph H. Torrence
*Attorney, Agent, or Firm*—Theresa Y. Cheng; Raymond M. Speer; Mario A. Monaco

[57] ABSTRACT

Novel substituted-benzyl derivatives of 11-endo-amino-5,6,7,8,9,10-hexahydro-2-hydroxy (or methoxy)-6,9-methanobenzocyclooctene (or nonene) of the formula:

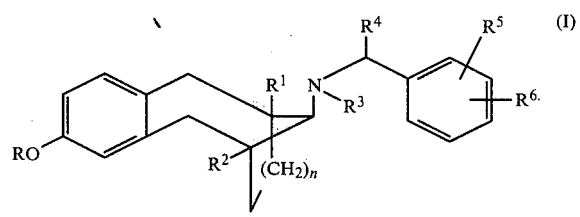

are centrally-acting analgesics effective in the relief of pain.

22 Claims, No Drawings

N-SUBSTITUTED-BENZYL-11-ENDO-AMINO-5,6,7,8,9,10-HEXAHYDRO-2-HYDROXY (OR METHOXY)-6,9-METHANOBENZOCYCLOOCTENE (OR NONENE) CENTRALLY-ACTING ANALGESICS

BACKGROUND OF THE INVENTION

1. Field of the Invention

The present invention is concerned with novel centrally-acting analgesic agents, i.e., agents acting on opiate receptors within the central nervous system to produce potent and profound analgesia.

The most widely used centrally-acting analgesic continues to be morphine. This drug, however, has serious drawbacks as the result of certain pronounced side effects. Not only does use of morphine usually lead to physiological and psychological dependency, but morphine is a respiratory depressant as well.

Thus, there has been a continuous search for a centrally-acting analgesic with the potency of morphine, but without its dangerous side effects. For example, many analgesic agents based on the morphine model have been prepared. One of the best known of these is meperidine. While this drug was originally thought to be non-addicting, it was soon found to have dangerous addiction liability.

Other centrally-acting analgesics include the class of compounds known as the benzomorphans. Pentazocine, phenazocine, cyclazocine, ketocyclazocine, and ethylketocyclazocine are some of the better known members of this class of compounds. However, as with other centrally-acting analgesics developed heretofore, the benzomorphans also have undesirable addiction qualities.

2. Brief Description of the Prior Art

Robinson et. al., U.S. Pat. Nos. 3,700,734; 3,514,463; 3,513,169; and 3,499,906 describe benzomorphan derivatives having analgesic activity.

Freed et. al., U.S. Pat. Nos. 3,836,670; 4,001,331; and 4,076,953 describe benzobicycloalkane amines for inducing analgesia.

Co-pending U.S. Ser. No. 117,701, filed Feb. 19, 1980, describes derivatives of 2-hydroxy-6,9-methano-11-amino-5,6,7,8,9,10-hexahydrobenzocyclooctene.

However, none of the compounds disclosed in any of the above would suggest the novel compounds of the present invention to a person of ordinary skill in the art.

SUMMARY OF THE INVENTION

The present invention relates to novel substituted-benzyl derivatives of 11-endo-amino-5,6,7,8,9,10-hexahydro-2-hydroxy (or methoxy)-6,9-methanobenzocyclooctene (or nonene) and pharmaceutically acceptable salts thereof.

The present invention also relates to a method of treating pain comprising administering to a patient (human or animal) in need of such treatment, a therapeutically effective amount of a novel compound of the present invention; as well as to a pharmaceutical composition for use in treating pain comprising a pharmaceutically acceptable carrier and a therapeutically effective amount of a novel compound of the present invention.

The present invention also relates to a method of preparing the novel compounds of the present invention.

The novel compounds of the present invention may be represented by the following formula:

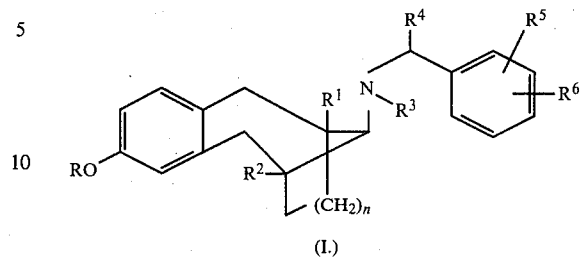

(I.)

where

R is hydrogen or methyl;

$R^1$, $R^2$, and $R^4$ are each independently selected from the group consisting of (1) hydrogen; and (2) $C_{1-4}$ alkyl;

$R^3$ is selected from the group consisting of (1) hydrogen; (2) $C_{1-4}$ alkyl; (3) $C_{1-4}$ alkenyl; (4) $C_{3-6}$ cycloalkyl; (5) $C_{3-4}$ cycloalkyl $C_{1-4}$ alkyl; (6) $C_{3-6}$ cycloalkenyl; (7) $C_{3-4}$ cycloalkenyl $C_{1-4}$ alkyl; (8) phenyl; (9) 5- and 6-membered heterocyclic wherein the heteroatom is nitrogen, oxygen, or sulfur, and said heterocyclic attached through $C_{1-2}$ alkyl; and (10) a methylene bridge attached to the phenyl moiety so as to form a dihydro isoindole structure with the nitrogen atom;

$R^5$ and $R^6$ are each independently selected from the group consisting of (1) hydrogen; (2) halo; (3) $C_{1-4}$ alkyl; (4) $C_{1-4}$ alkoxy; (5) amino, and mono- and di-$C_{1-4}$ alkyl substituted amino; (6) cyano; (7) trifluoromethyl; (8) trifluoromethylthio; (9) $C_{1-4}$ alkylthio; (10) $C_{1-4}$ alkylsulfoxide; (11) $C_{1-4}$ alkylsulfone; (12) hydroxy; and (13) phenyl; and n is 1 or 2; and a pharmaceutically acceptable salt thereof.

When n is 1, the benzocyclooctene structure is represented. Where n is 2, the structure is a 5(H)-6,7,8,9,10,11-hexahydro-2-hydroxy (or methoxy)-6,10-methanobenzocyclononene. These structures, and their respective numberings, may be illustrated as follows:

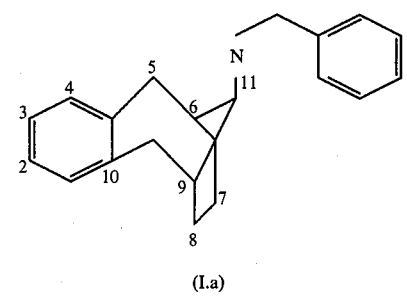

(I.a)

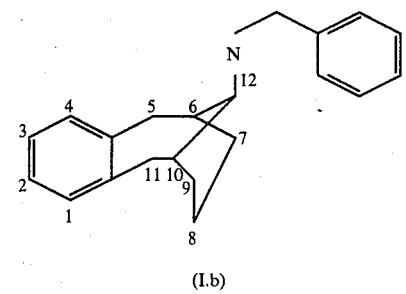

(I.b)

Included in this invention are the optical isomers of the compounds of Formula I, which may vary to some extent in their biological activity.

These isomers can be separated into their optical isomers [dextro (+) and levo (−)] by preparing the diastereoisomeric salts with optically active acids, either D (+) or L (−), which salts can then be separated by conventional methods such as fractional crystallization. Thus, it is to be understood that included in this invention, in addition to racemic mixtures of the novel N-substituted-benzyl-11-endo-amino-5,6,7,8,9,10-hexahydro-2-hydroxy (or methoxy)-6,9-methanobenzocyclooctene (or nonene) compounds, are the individual optical isomers, i.e., the dextrorotatory (+) and levorotatory (−) isomers of said novel compounds.

Among the novel compounds of the present invention, certain compounds are preferred. For example, the phenyl moiety substituents, $R^5$ and $R^6$, are preferred in the following order: para, meta, ortho.

It is preferred that the $R^1$, $R^2$, $R^3$ and $R^4$ substituents be hydrogen.

The following phenyl moiety substituents are preferred: hydrogen, p-methoxy, p-chloro, p-dimethylamino, and p-methyl.

Representative compounds of the present invention are:

N-(4-chlorobenzyl)-5,6,7,8,9,10-hexahydro-11-endo-amino-2-methoxy-6,9-methanobenzocyclooctene;
N-(4-chlorobenzyl)-N-methyl-5,6,7,8,9,10-hexahydro-11-endo-amino-6,9-methanobenzocycloocten-2-ol;
N-(4-methoxybenzyl)-5,6,7,8,9,10-hexahydro-11-endo-amino-6,9-methanobenzocycloocten-2-ol;
N-(4-hydroxybenzyl)-5,6,7,8,9,10-hexahydro-11-endo-amino-6,9-methanobenzocycloocten-2-ol;
N-(4-phenylbenzyl)-5,6,7,8,9,10-hexahydro-11-endo-amino-6,9-methanobenzocycloocten-2-ol;
N-(4-dimethylaminobenzyl)-5,6,7,8,9,10-hexahydro-11-endo-amino-6,9-methanobenzocycloocten-2-ol;
N-(4-fluorobenzyl)-5,6,7,8,9,10-hexahydro-11-endo-amino-6,9-methanobenzocycloocten-2-ol;
N-(4-propoxybenzyl)-5,6,7,8,9,10-hexahydro-11-endo-amino-6,9-methanobenzocycloocten-2-ol;
N-(3-methoxybenzyl)-5,6,7,8,9,10-hexahydro-11-endo-amino-6,9-methanobenzocycloocten-2-ol;
N-(3-cyanobenzyl)-5,6,7,8,9,10-hexahydro-11-endo-amino-6,9-methanobenzocycloocten-2-ol;
N-(3-hydroxybenzyl)-5,6,7,8,9,10-hexahydro-11-endo-amino-6,9-methanobenzocycloocten-2-ol;
N-(3,4-dimethoxybenzyl)-5,6,7,8,9,10-hexahydro-11-endo-amino-6,9-methanobenzocycloocten-2-ol;
N-(4-cyanobenzyl)-5,6,7,8,9,10-hexahydro-11-endo-amino-6,9-methanobenzocycloocten-2-ol;
N-(4-methylbenzyl)-5,6,7,8,9,10-hexahydro-11-endo-amino-6,9-methanobenzocycloocten-2-ol;
N-(2-methoxybenzyl)-5,6,7,8,9,10-hexahydro-11-endo-amino-6,9-methanobenzocycloocten-2-ol;
N-(4-bromobenzyl)-5,6,7,8,9,10-hexahydro-11-endo-amino-6,9-methanobenzocycloocten-2-ol;
N-phenyl-5,6,7,8,9,10-hexahydro-11-endo-amino-6,9-methanobenzocycloocten-2-ol;
N-(4-chlorobenzyl)-5,6,7,8,9,10-hexahydro-11-endo-amino-6,9-methanobenzocycloocten-2-ol;

Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Water or oil-soluble or dispersible products are thereby obtained.

The novel compounds of the present invention are useful in alleviating pain in animal and human patients. For example, compounds of Formula I show good activity in a modified Randall Selitto test. Good activity in this test is accepted in the art as indicative of useful analgesic activity.

In addition, the compounds of the present invention show a reduction in the severity of the serious side effects associated with members of the morphine family of naturally occurring alkaloidal analgesics, such as addiction, tolerance, and respiratory depression. Moreover, unlike the morphine analgesics, the compounds of the present invention are orally active.

Various tests in animals have been carried out to show the ability of the compounds of this invention to exhibit reactions that can be correlated with activity in humans. One such test, outlined by Winter and Flataker in *J. Phar. Exp. Tera.*, 150, 1, pp. 165–171, shows the ability of the compounds of Formula I to exhibit analgesic effect. Measurements are made of the reaction threshold to pressure in the hind paws of rats injected with a phlogistic agent. These are compared with known analgesic drugs, and marked increased effects can be found. Drug dosages of up to 64 mg/kg are administered by the subcutaneous route. The experiments are carried out on Sprague-Dawley female rats weighing from 60 to 80 grams. The response threshold is determined by applying pressure to the foot and reading on a manometer the pressure at which an audible "squeak" is elicited. Groups of ten rats are used for each test and the average reading is recorded.

Thus, the novel compounds of Formula I possess a high degree of analgesic activity, and are, accordingly, useful in treating animal and human patients experiencing moderate to severe pain originating from any one of a number of different sources.

The novel compounds of Formula I are also useful as anti-diarrheal and anti-tussive agents.

For these purposes the compounds of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alignic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example calcium carbonate, calcium phosphate or kaolin, or as soft gelatine capsules wherein the active ingedient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the analgesic agents are employed.

Dosage levels of the order of 5 to 50 mg per day are useful in the treatment of the above indicated conditions. For example, analgesic activity is manifested by the administration of from about 0.1 to 1.0 milligrams of the compound per kilogram of body weight per day. Advantageously from about 0.05 mg to about 0.5 mg per kilogram of body weight per daily dosage produce highly effective results.

The amount of active ingredient that may be combined with the carrier materials to produce a single dosage form will vary depending upon the host treated and the particular mode of administration. For example, a formulation intended for the oral administration of humans may contain from 5 to 50 mg of active agent compounded with an appropriate and convenient amount of carrier material which may vary from about 5 to about 95 percent of the total composition. Dosage unit forms will generally contain between from about 2 mg to about 15 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The novel compounds of Formula I are conveniently prepared by the following method from known starting materials.

The starting materials are 5,6,7,8,9,10-hexahydro-6,9-methanobenzocyclooctene-11-ones and are readily prepared by the reaction of α,α'-dihalo xylene or an appropriately substituted xylene and a cyclic ketone derivative. Thus, for example, reaction of α,α'-dibromo xylene and the pyrrolidine enamine of cyclopentanone or cyclohexanone in an aprotic solvent such as acetonitrile produces the desired 6,9-methanobenzocyclooctene-11-one or the corresponding benzocyclononen-11-one. In order to introduce the phenolic hydroxyl group into the cyclooctene-11-one compounds in a one-step reaction, the starting ketone is treated in strongly acid solution, preferably in trifluoroacetic acid, with thallium trifluoroacetate at a temperature of from 0°–50° C. and preferably between 10°–30° C. The reaction is allowed to proceed for a period of from 1–24 hours and is then treated with an oxidizing agent, as for example lead tetraacetate, and the resulting mixture is then stirred with heating, preferably at reflux temperature of the reaction mixture for a period of from 1–5 hours. The entire reaction mixture is then treated with triphenyl phosphine in order to free the hydroxy cyclooctene-11-one from its complex, and then the desired ketone purified by removal of the reaction solvent by evaporation under reduced pressure followed by extraction of the residual material with chloroform, and the chloroform extract washed with water and dried to yield the desired product, which is conveniently purified by crystallization from a solvent.

The phenolic hydroxyl compound prepared as just described can then be converted to the corresponding methoxy compound by reaction with a methylating agent such as dimethylsulfate or methyl iodide in the presence of a base such as potassium carbonate.

The hydroxy or methoxy 11-keto compounds prepared according to the previous procedure are readily converted to the corresponding 11-amino compounds by conversion to the corresponding oximes, followed by catalytic reduction to the amine. Thus, for example, D,L-5,6,7,8,9,10-hexahydro-2-hydroxy-6,9-methanobenzocyclooctene-11-one is converted to the corresponding 11-oximino compound by refluxing in the presence of an approximately equimolar amount of hydroxylamine hydrochloride. Following formation of the oxime, the reaction mixture is diluted with water and extracted to isolate the oxime, which is then further purified by chromatography on silica gel, followed by elution with chloroform containing traces of methanol. The oxime thus isolated is reduced, for example with hydrogen in the presence of a catalyst such as platinum oxide, to give the 11-amino compound, which is then purified by chromatography.

Once the 11-amino compounds are obtained, they are reductively alkylated with aldehydes using sodium cyanoborohydride. This reaction may be illustrated as follows:

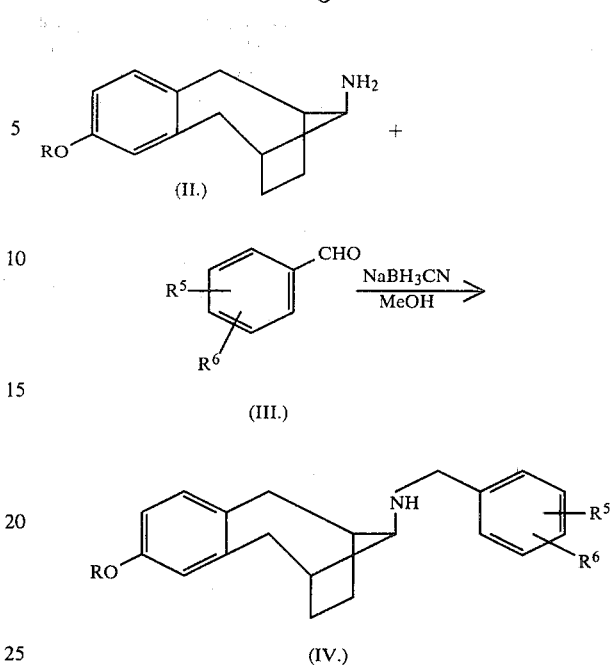

In a typical procedure, 10 mmoles of the amine (II) are dissolved in 140 ml of methanol, and 100 mmoles of the appropriately substituted aldehyde (III) and 40 mmoles of sodium cyanoborohydride are added. The resulting mixture is stirred at room temperature, and the course of the reaction is followed by thin layer chromatography (TLC). Most of the methanol is removed under vacuum and the residue is taken up in water. Extraction with 5% methanol/chloroform yields a crude mixture. The product (IV) is obtained by chromatography on a silica gel column eluting with 5% methanol in chloroform. The hydrochloride salt is prepared by bubbling hydrochloride gas through a solution of the product in chloroform and precipitating the salt with ether.

A process for the preparation of the compounds of the present invention which are substituted by alkyl substituents, e.g., methyl substituents in the 6 and/or 9 positions, begins with the treatment of an α,α-dihaloxylene with an alkylated or dialkylated derivative of the appropriate cycloalkanone-enamine. Thus, for example, α,α-dibromoxylene is treated with the pyrrolidine enamine of 2,5-dimethylcyclopentanone to produce the corresponding 6,9-dimethyl-5,6,7,8,9,10-hexahydro-6,9-methanobenzocyclooctene-11-one, followed by thallation as described hereinabove, to introduce the corresponding 2'-hydroxy compound and subsequent conversion to the oxime, followed by catalytic reduction to the desired D,L-11-endo-amino-6,9-dimethyl-5,6,7,8,9,10-hexahydro-6,9-methanobenzocyclooctene.

Another method of preparing the novel compounds of Formula I is by treating a bicyclic ketone starting material prepared as described above, with an appropriately substituted benzyl amine. The reaction sequence may be illustrated as follows:

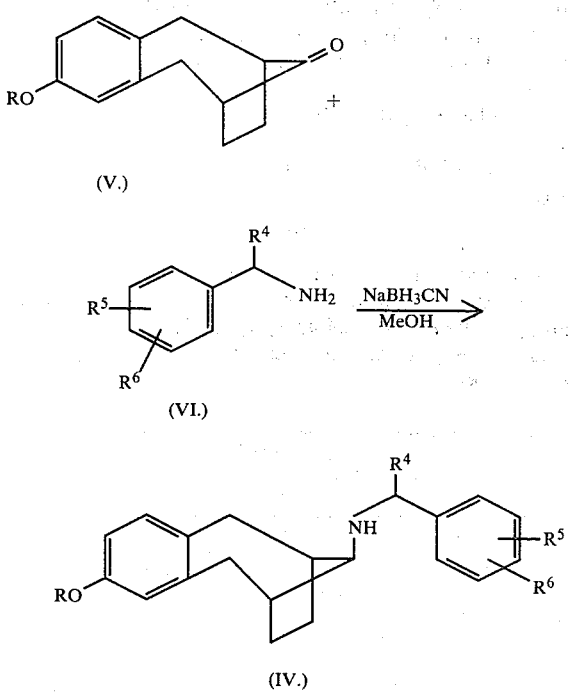

Yet another method of preparing the novel compounds of Formula I is by alkylation of the amine (II) with an appropriately substituted benzyl halide (VII). The reaction sequence for this method may be illustrated as follows:

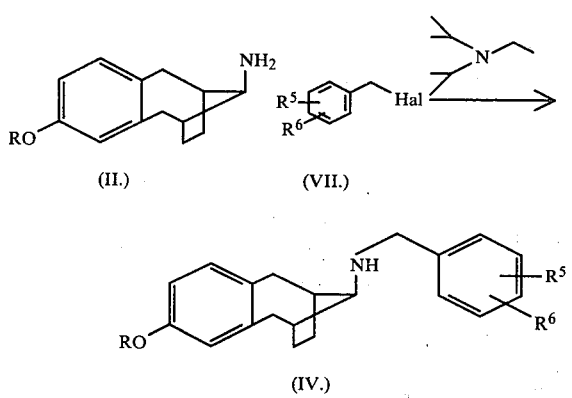

In a typical procedure for this method, 10 mmoles of amine (II) in 150 ml of tetrahydrofuran has added to it 10 mmoles of appropriately substituted benzyl bromide and 3 ml of diisopropylethylamine. The mixture is refluxed for 3 hours, after which it is evaporated to dryness; and the residue is then taken up in water and extracted three times with methylene chloride. The organic layer is dried and evaporated to dryness. The residue is absorbed on a silica gel column and elution with 5% methanol/chloroform yields the desired product.

The following examples illustrate preparation of various of the novel compounds of the present invention, but are not intended to in any way be a limitation thereof.

EXAMPLE 1

N-(4-Cyanobenzyl)-5,6,7,8,9,10-hexahydro-11-endo-amino-6,9-methanobenzocycloocten-2-ol hydrochloride To 150 ml of tetrahydrofuran there is added 4.0 g of 11-endo-amino-5,6,7,8,9,10-hexahydro-6,9-methanobenzocycloocten-2-ol, followed by 4.0 g of α-bromo-p-tolunitrile and 3 ml of diisopropylethylamine. The reaction mixture is refluxed for 3 hours, then evaporated to dryness. The residue is taken up in 100 ml of water, then extracted three times with dichloromethane. The organic layer is dried and evaporated, and the residue is absorbed on a silica gel column, eluting with 5% methanol in chloroform, to give the free base which is treated with hydrogen chloride gas to give 2.4 g of the title compound, m.p. 295°–297° C. Analysis:

Calculated for $C_{21}H_{23}N_2Cl$: % C, 71.07; % H, 6.53; % N, 7.98; % Cl, 9.99;

Found: % C, 70.72; % H, 6.90; % N, 7.43; % Cl, 10.11.

EXAMPLE 2

N-[4-(Trifluoromethylthio)benzyl]-5,6,7,8,9,10-hexahydro-11-endo-amino-6,9-methanobenzocycloocten-2-ol maleate Following the procedures of Example 1 above, but substituting 1.354 g (5.0 mmoles) of α-bromo-p-trifluoromethylthio-toluene, there is prepared the title compound, m.p. 155°–160° C., by treating the free base with an equivalent of maleic acid. Analysis:

Calculated: % C, 58.89; H, 5.14; % N, 2.74; % F, 11.17;

Found: % C, 59.02; H, 5.55; % N, 2.69; % F, 10.67.

EXAMPLE 3

N-(4-Chlorobenzyl)-N-methyl-5,6,7,8,9,10-hexahydro-11-endo-amino-6,9-methanobenzocycloocten-2-ol

Step A

N-(4-Chlorobenzyl)-5,6,7,8,9,10-hexahydro-11-endo-amino-2-methoxy-6,9-methanobenzocyclooctene hydrochloride There is mixed together at room temperature in 200 ml of methanol 4.4 g of 11-endo-amino-5,6,7,8,9,10-hexahydro-2-methoxy-6,9-methanobenzocyclooctene hydrochloride and 13.0 g of p-chlorobenzaldehyde. There is then added 5.0 g of sodium cyanoborohydride in portions, and the reaction mixture is allowed to stand overnight. Most of the methanol is removed under vacuum and the residue is taken up in 200 ml of water, after which 5% sodium bicarbonate is added and extraction with chloroform takes place. The free base is obtained by chromatography on a silica gel column, eluting with 10% hexane/ether, and is then treated with hydrogen chloride gas to give 1.5 g of the title compound, m.p. 235°–237° C. Analysis:

Calculated: % C, 66.60; % H, 6.66; % N, 3.70; % Cl, 18.74

Found: % C, 66.39; % H, 6.59; % N, 3.74; % Cl, 19.02.

Step B
N-(4-Chlorobenzyl)-N-methyl-5,6,7,8,9,10-hexahydro-11-endo-amino-2-methoxy-6,9-methanobenzocyclooctene To 50 ml of tetrahydrofuran there is added 1.0 g of the product prepared in Step A above, followed by 0.5 g of methyliodide. The reaction mixture is heated at reflux for 1 hour, after which it is evaporated to dryness. The residue is taken up in 20 ml of water, followed by extraction three times with dichloromethane. The organic layer is dried over sodium sulfate and evaporated to give 1.0 g of product, which is utilized directly in the next step.

Step C
N-(4-chlorobenzyl)-N-methyl-5,6,7,8,9,10-hexahydro-11-endo-amino-6,9-methanobenzocycloocten-2-ol hydrochloride The product prepared in Step B above is dissolved in 25 ml of 48% hydrobromic acid and 25 ml of acetic acid, and the reaction mixture is then heated at reflux for 2 hours. The reaction mixture is neutralized with sodium bicarbonate, after which 25 ml of water is added, followed by extraction with dichloromethane, drying, and evaporation. There is obtained the free base, which is then treated with hydrogen chloride gas to give 1.0 g of the title compound, m.p. 265°–270° C.
Analysis:
Calculated: % C, 66.67; % H, 6.66; % N, 4.23; % Cl, 18.74
Found: % C, 66.44; % H, 6.92; % N, 3.96; % Cl, 18.67.

EXAMPLE 4
N-(4-methylbenzyl)-5,6,7,8,9,10-hexahydro-11-endo-amino-6,9-methanobenzocycloocten-2-ol hydrochloride There is added to 150 ml of methanol, 2.0 g of 11-endo-amino-5,6,7,8,9,10-hexahydro-6,9-methanobenzocycloocten-2-ol and 2.5 g of p-methylbenzaldehyde. The mixture is stirred at room temperature for 5 minutes, after which 2.5 g of sodium cyanoborohydride is added. The reaction mixture is then stirred overnight at room temperature. Most of the methanol is removed under vacuum and the residue is taken up in 100 ml of water. There is added 100 ml of 1 N sodium bicarbonate, followed by extraction with chloroform, drying and evaporation. The hydrochloride salt is prepared by bubbling hydrogen chloride gas through a solution of the amine in chloroform and precipitating the salt with ether. Yield is 1.4 g of the title compound, m.p. 255° C.
Analysis:
Calculated: % C, 73.35; % H, 7.62; % N, 4.07; % Cl, 10.30
Found: % C, 73.15; % H, 7.75; % N, 3.94; % Cl, 10.07.

EXAMPLES 5–17

Following the procedures described in Example 4 above, but substituting for the p-methylbenzaldehyde an equivalent amount of an appropriate benzaldehyde, there is prepared the following compounds of the present invention:

| Exp. No. | SUBSTITUENT $R^5$, $R^6$ | MELTING POINT °C. | CALCULATED C | H | N | Cl | FOUND C | H | N | Cl |
|---|---|---|---|---|---|---|---|---|---|---|
| 5 | p-OCH$_3$ | 271–273 (dec) | 70.08; | 7.28; | 3.89; | 9.85 | 69.91; | 7.34; | 3.88; | 9.67 |
| 6 | p-OH$^a$ | 240 (dec) | 66.11; | 7.16; | 3.85 | | 66.14; | 7.14; | 3.77 | |
| 7 | p-C$_6$H$_5$$^b$ | 300 (dec) | 75.43; | 6.80; | 3.37 | | 75.47; | 7.13; | 3.39 | |
| 8 | p-NMe$_2$$^c$ | 210 (dec) | 59.32; | 7.64; | 6.29; | 15.93 | 59.37; | 7.55; | 6.45; | 15.45 |
| 9 | p-F | 297–299 (dec) | 69.07; | 6.66; | 4.03 | | 69.28; | 6.70; | 4.00 | |
| 10 | p-OC$_3$H$_7$ | 237–239 (dec) | 67.77; | 7.23; | 3.59; | 9.09 | 67.23; | 7.34; | 3.52; | 8.97 |
| 11 | m-CH$_3$O | 257–260 (dec) | 70.08; | 7.28; | 9.85; | 3.89 | 69.95; | 7.53; | 9.73; | 3.77 |
| 12 | m-CN | 201–202 (dec) | 71.07; | 6.53; | 7.98; | 9.99 | 70.83; | 6.52; | 8.24; | 9.64 |
| 13 | m-OH$^b$ | 265–267 (dec) | 67.80; | 7.00; | 3.90; | 10.00 | 67.97; | 7.16; | 3.87; | 10.08 |
| 14 | 3,4-(MeO)$_2$ | 260–262 | 67.70; | 7.23; | 3.59; | 9.09 | 67.23; | 7.34; | 3.52; | 8.98 |
| 15 | p-CN | 295–297 | 71.07; | 6.53; | 7.88; | 9.99 | 70.72; | 6.90; | 7.43; | 10.11 |
| 16 | o-OMe | 255–257 | 70.08; | 7.28; | 3.89; | 9.85 | 70.34; | 7.55; | 3.87; | 9.86 |
| 17 | p-Br | 260–262 | 58.76; | 5.67; | 3.42; | 19.54 Br: 19.54 | 59.06; | 6.08; | 3.37; | 8.02 Br: 19.12 |

$^a$Analysis calculated for monohydrate
$^b$Analysis calculated for himihydrate
$^c$Analysis calculated for dihydrate

What is claimed is:
1. A compound of the formula:

$$\text{(I)}$$

where
R is hydrogen or methyl;
$R^1$, $R^2$ and $R^4$ are each independently selected from the group consisting of (1) hydrogen; and (2) $C_{1-4}$alkyl;
$R^3$ is selected from the group consisting of (1) hydrogen; (2) $C_{1-4}$alkyl; (3) $C_{1-4}$alkenyl; (4) $C_{3-6}$cycloalkyl; (5) $C_{3-4}$cycloalkyl $C_{1-4}$alkyl; (6) $C_{3-6}$cycloalkenyl; (7) $C_{3-4}$cycloalkenyl $C_{1-4}$alkyl; (8) phenyl; and (9) a methylene bridge attached to the phenyl moiety so as to form a dihydro isoindole structure with the nitrogen atom;
$R^5$ and $R^6$ are each independently selected from the group consisting of (1) hydrogen; (2) halo; (3) $C_{1-4}$alkyl; (4) $C_{1-4}$alkoxy; (5) amino, and mono- and di-$C_{1-4}$alkyl substituted amino; (6) cyano; (7) trifluoromethyl; (8) trifluoromethylthio; (9) $C_{1-4}$alkylthio; (10) $C_{1-4}$alkylsulfoxide; (11) $C_{1-4}$alkylsulfone; (12) hydroxy; and (13) phenyl; and n is 1 or 2; and a pharmaceutically acceptable salt thereof.

2. A compound according to claim 1 wherein the compound is N-(4-chlorobenzyl)-5,6,7,8,9,10-hexahydro-11-endo-amino-2-methoxy-6,9-methanobenzocyclooctene.

3. A compound according to claim 1 wherein the compound is N-(4-chlorobenzyl)-N-methyl-5,6,7,8,9,10-hexahydro-11-endo-amino-6,9-methanobenzocycloocten-2-ol.

4. A compound according to claim 1 wherein the compound is N-(4-methoxybenzyl)-5,6,7,8,9,10-hexahydro-11-endo-amino-6,9-methanobenzocycloocten-2-ol.

5. A compound according to claim 1 wherein the compound is N-(4-hydroxybenzyl)-5,6,7,8,9,10-hexahydro-11-endo-amino-6,8-methanobenzocycloocten-2-ol.

6. A compound according to claim 1 wherein the compound is N-(4-phenylbenzyl)-5,6,7,8,9,10-hexahydro-11-endo-amino-6,9-methanobenzocycloocten-2-ol.

7. A compound according to claim 1 wherein the compound is N-(4-dimethylaminobenzyl)-5,6,7,8,9,10-hexahydro-11-endo-amino-6,9-methanobenzocycloocten-2-ol.

8. A compound according to claim 1 wherein the compound is N-(4-fluorobenzyl)-5,6,7,8,9,10-hexahydro-11-endo-amino-6,9-methanobenzocycloocten-2-ol.

9. A compound according to claim 1 wherein the compound is N-(4-propoxybenzyl)-5,6,7,8,9,10-hexahydro-11-endo-amino-6,9-methanobenzocycloocten-2-ol.

10. A compound according to claim 1 wherein the compound is N-(3-methoxybenzyl)-5,6,7,8,9,10-hexahydro-11-endo-amino-6,9-methanobenzocycloocten-2-ol.

11. A compound according to claim 1 wherein the compound is N-(3-cyanobenzyl)-5,6,7,8,9,10-hexahydro-11-endo-amino-6,9-methanobenzocycloocten-2-ol.

12. A compound according to claim 1 wherein the compound is N-(3-hydroxybenzyl)-5,6,7,8,9,10-hexahydro-11-endo-amino-6,9-methanobenzocycloocten-2-ol.

13. A compound according to claim 1 wherein the compound is N-(3,4-dimethoxybenzyl)-5,6,7,8,9,10-hexahydro-11-endo-amino-6,9-methanobenzocycloocten-2-ol.

14. A compound according to claim 1 wherein the compound is N-(4-cyanobenzyl)-5,6,7,8,9,10-hexahydro-11-endo-amino-6,9-methanobenzocycloocten-2-ol.

15. A compound according to claim 1 wherein the compound is N-(4-methylbenzyl)-5,6,7,8,9,10-hexahydro-11-endo-amino-6,9-methanobenzocycloocten-2-ol.

16. A compound according to claim 1 wherein the compound is N-(2-methoxybenzyl)-5,6,7,8,9,10-hexahydro-11-endo-amino-6,9-methanobenzocycloocten-2-ol.

17. A compound according to claim 1 wherein the compound is N-(4-bromobenzyl)-5,6,7,8,9,10-hexahydro-11-endo-amino-6,9-methanobenzocycloocten-2-ol.

18. A compound according to claim 1 wherein the compound is N-phenyl-5,6,7,8,9,10-hexahydro-11-endo-amino-6,9-methanobenzocycloocten-2-ol.

19. A compound according to claim 1 wherein the compound is N-(4-chlorobenzyl)-5,6,7,8,9,10-hexahydro-11-endo-amino-6,9-methanobenzocycloocten-2-ol.

20. A method of treating pain comprising administering to a patient in need of such treatment a therapeutically effective amount of a compound of the formula:

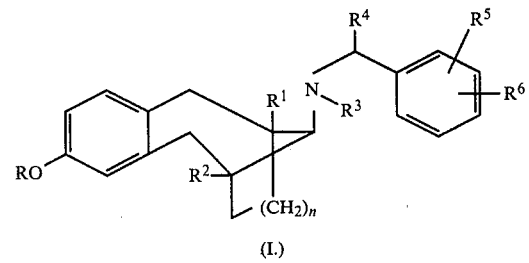

(I.)

where
R is hydrogen or methyl;
$R^1$, $R^2$, and $R^4$ are each independently selected from the group consisting of (1) hydrogen; and (2) $C_{1-4}$alkyl;
$R^3$ is selected from the group consisting of (1) hydrogen; (2) $C_{1-4}$alkyl; (3) $C_{1-4}$alkenyl; (4) $C_{3-6}$cycloalkyl; (5) $C_{3-4}$cycloalkyl $C_{1-4}$alkyl; (6) $C_{3-6}$cycloalkenyl; (7) $C_{3-4}$cycloalkenyl $C_{1-4}$alkyl; (8) phenyl; and (9) a methylene bridge attached to the phenyl moiety so as to form a dihydro isoindole structure with the nitrogen atom;
$R^5$ and $R^6$ are each independently selected from the group consisting of (1) hydrogen; (2) halo; (3) $C_{1-4}$alkyl; (4) $C_{1-4}$alkoxy; (5) amino, and mono- and di-$C_{1-4}$alkyl substituted amino; (6) cyano; (7) trifluoromethyl; (8) trifluoromethylthio; (9) $C_{1-4}$alkylthio; (10) $C_{1-4}$alkylsulfoxide; (11) $C_{1-4}$alkylsulfone; (12) hydroxy; and (13) phenyl; and
n is 1 or 2; and a pharmaceutically acceptable salt thereof.

21. A method according to claim 20 wherein the amount administered is from 5 to 50 mg per day.

22. A pharmaceutical composition for use in treating pain comprising a pharmaceutically acceptable carrier and a therapeutically effective amount of a compound of the formula:

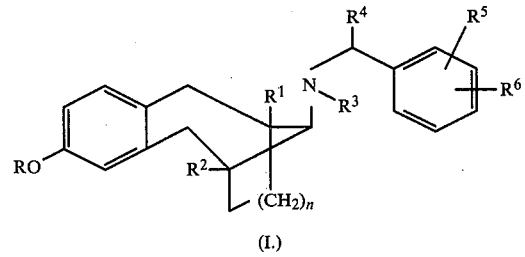

(I.)

where
R is hydrogen or methyl;
$R^1$, $R^2$, and $R^4$ are each independently selected from the group consisting of (1) hydrogen; and (2) $C_{1-4}$ alkyl;
$R^3$ is selected from the group consisting of (1) hydrogen; (2) $C_{1-4}$alkyl; (3) $C_{1-4}$alkenyl; (4) $C_{3-6}$cycloalkyl; (5) $C_{3-4}$cycloalkyl $C_{1-4}$alkyl; (6) $C_{3-6}$cycloalkenyl; (7) $C_{3-4}$cycloalkenyl $C_{1-4}$alkyl; (8) phenyl; and (9) a methylene bridge attached to the phenyl moiety so as to form a dihydro isoindole structure with the nitrogen atom;
$R^5$ and $R^6$ are each independently selected from the group consisting of (1) hydrogen; (2) halo; (3) $C_{1-4}$alkyl; (4) $C_{1-4}$alkoxy; (5) amino, and mono- and di-$C_{1-4}$alkyl substituted amino; (6) cyano; (7) trifluoromethyl; (8) trifluoromethylthio; (9) $C_{1-4}$alkylthio; (10) $C_{1-4}$alkylsulfoxide; (11) $C_{1-4}$alkylsulfone; (12) hydroxy; and (13) phenyl; and
n is 1 or 2; and a pharmaceutically acceptable salt thereof.

* * * * *